United States Patent [19]

Tsao

[11] 3,992,460

[45] Nov. 16, 1976

[54] PURGING OF TARS AND CARBON FROM CHLORINATED HYDROCARBON EFFLUENT

[75] Inventor: Utah Tsao, Jersey City, N.J.

[73] Assignee: The Lummus Company, Bloomfield, N.J.

[22] Filed: July 15, 1974

[21] Appl. No.: 488,459

Related U.S. Application Data

[63] Continuation-in-part of Ser. No. 238,196, March 27, 1972, Pat. No. 3,968,200.

[52] U.S. Cl. .................. 260/654 R; 260/656 R; 260/658 R; 260/660; 260/659 R
[51] Int. Cl.² .................................... C07C 21/00
[58] Field of Search ..... 260/656 R, 652 P, DIG. 42, 260/659 R, 654 R, 658 R, 660

[56] References Cited

UNITED STATES PATENTS

| | | | |
|---|---|---|---|
| 2,377,669 | 6/1945 | Brown et al. | 260/658 R |
| 2,727,076 | 12/1955 | Warren | 260/658 R |
| 3,055,955 | 9/1962 | Hodges | 260/656 R |
| 3,647,358 | 3/1972 | Greenberg | 423/210.5 |
| 3,879,481 | 4/1975 | Sze et al. | 260/656 R |

FOREIGN PATENTS OR APPLICATIONS

| | | | |
|---|---|---|---|
| 1,062,815 | 3/1967 | United Kingdom | 260/658 R |

Primary Examiner—Delbert E. Gantz
Assistant Examiner—Joseph A. Boska
Attorney, Agent, or Firm—Marn & Jangarathis

[57] ABSTRACT

An effluent containing chlorinated hydrocarbons and tar, withdrawn from a reactor employing molten copper chlorides and oxychloride, is quenched to separate carbon and tars, and the separated carbon and tars introduced into the reactor to effect combustion thereof. The reaction is preferably directed to the production of vinyl chloride or chlorinated methanes.

6 Claims, 1 Drawing Figure

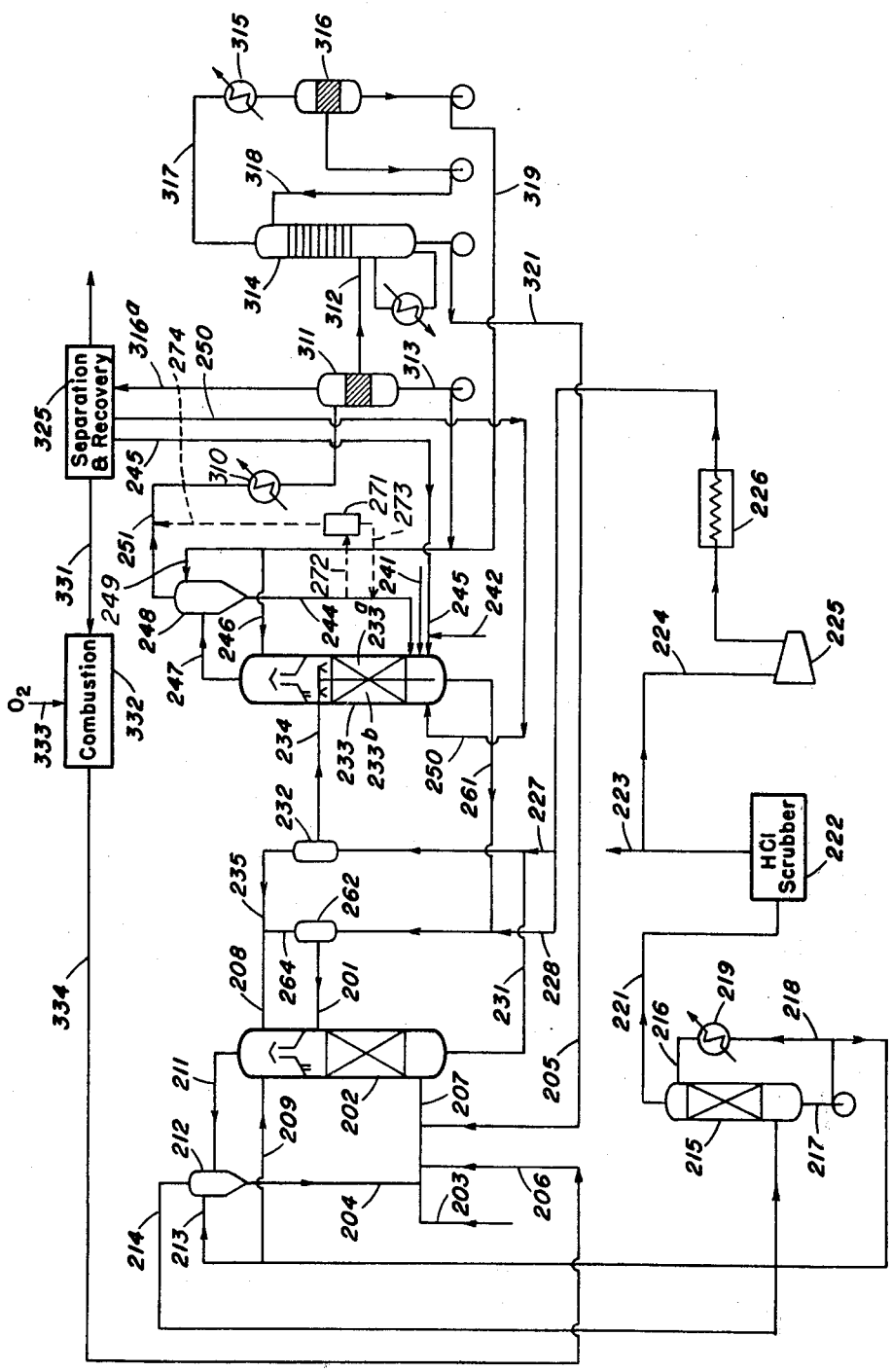

PURGING OF TARS AND CARBON FROM CHLORINATED HYDROCARBON EFFLUENT

This application is a continuation-in-part of application Ser. No. 238,196, filed on Mar. 27, 1972, now U.S. Pat. No. 3,968,200.

This invention relates to the treatment of an effluent containing chlorinated hydrocarbons, and more particularly to a new and improved process for purging tars and carbons from an effluent containing chlorinated hydrocarbons.

In the chlorination of a hydrocarbon, or partially chlorinated hydrocarbon, the chlorination effluent generally includes tars and carbons which are carried into the separation and recovery system for separating and recovering the various components of the chlorination effluent. In such processes, the tar and carbon materials may cause difficulties in the separation and recovery system. In addition, processing steps must be effected to purge the system of such tars and carbon.

Accordingly, the principle object of the present invention is to provide a new and improved process for purging tars and carbon from an effluent containing chlorinated hydrocarbons.

In accordance with the present invention, tars and carbon are separated from an effluent containing chlorinated hydrocarbons, withdrawn from a melt chlorination and/or dehydrochlorination reaction zone, and the separated tars and carbon are directly contacted with a molten mixture, containing the higher and lower valent chlorides of a multivalent metal and the oxychloride of the metal to effect oxidation of the tars and carbon. In this manner, the tars and carbon are effectively purged from the system without being passed through the separation and recovery system for recovering the various chlorinated hydrocarbons.

The effluent, containing chlorinated hydrocarbons, carbon and tars is generally one produced by contacting, in a chlorination (oxychlorination) zone, a hydrocarbon or partially chlorinated hydrocarbon with chlorine and/or hydrogen chloride, and a melt containing the higher and lower valent chlorides of a multivalent metal and the oxychloride of the multivalent metal. Accordingly, the separated tars and carbons may be conveniently oxidized by introducing the separated tars and carbon into the chlorination (oxychlorination)-reaction zone. It is to be understood, however, that oxidation of separated tars and carbon by direct contact with the hereinabove described molten salt could be effected in a separate reaction zone designed and operated for the purpose of oxidizing such separated tars or in a reaction zone other than the chlorination reaction zone, in which there is present the hereinabove described molten salt.

The hydrocarbon or partially chlorinated hydrocarbon employed as feed to the chlorination reaction zone may be: an aromatic hydrocarbon, such as benzene; an aliphatic hydrocarbon (saturated or olefinically unsaturated), preferably a $C_1$ to $C_4$ aliphatic hydrocarbon; or a partially chlorinated derivative of such aromatic and aliphatic hydrocarbons. The most preferred feeds are: ethane, ethylene, methane and the partially chlorinated $C_2$ hydrocarbons.

The process of the present invention is also applicable to the treatment of an effluent containing chlorinated hydrocarbons produced by the dehydrochlorination of a chlorinated hydrocarbon by direct contact with a molten salt mixture, containing the higher and lower valent chlorides of a multivalent metal, which may further include the oxychloride of the multivalent metal.

The chlorides of the multivalent metals used in forming the melt employed in the present invention for oxidation of tars and carbon, chlorination and dehydrochlorination are generally the chlorides of manganese, iron, copper, cobalt or chromium, preferably copper. The molten mixture generally also includes a metal salt melting point depressant which is non-volatile and resistant to oxygen at the process conditions, such as chloride of a univalent metal; i.e., a metal having only one positive valence state, to provide a salt mixture having a reduced melting point. The univalent metal chlorides are preferably alkali metal chlorides, such as potassium and lithium chloride, in particular, but it is to be understood that other metal chlorides and mixtures thereof, such as the heavy metal chlorides; i.e., heavier than copper, of Groups I, II, III and IV of the Periodic Table; e.g., zinc silver and thallium chloride, may also be employed. A preferred composition is formed from copper chlorides and potassium chloride with the potassium chloride comprising from about 20% to about 40%, by weight, of the composition with the remainder being copper chlorides.

In accordance with the present invention, the effluent withdrawn from the melt chlorination zone is at a temperature from about 700° F. to about 1200° F., with the specific temperature being dependent upon the feed being chlorinated and the products desired. The chlorination effluent, containing tars and carbons, is then cooled to a temperature at which a portion of the chlorinated hydrocarbon stream, including tars and carbon, is condensed. In general, the chlorinated hydrocarbon effluent is cooled to a temperature of from about 100° F. to about 300° F., preferably a temperature of from about 150° F. to about 280° F., and most preferably a temperature of from about 180° F. to about 240° F., at which temperature a portion of the chlorinated hydrocarbon stream, including the tars and carbon, is condensed. In general, such condensation is effected at a pressure from about 0 to about 100 psig., preferably from about 25 to about 60 psig. The cooling of the effluent to effect such condensation is preferably effected by direct contact quenching with a suitable quench liquid, such as a chlorinated hydrocarbon (the chlorinated hydrocarbon quench is preferably one or more of the chlorinated hydrocarbons recovered from the effluent).

The chlorinated hydrocarbon effluent condensate, containing tars and carbon, is then oxidized by direct contact with a molten salt mixture, containing the higher and lower valent chlorides of a multivalent metal and the oxychloride of the multivalent metal with the oxidation as hereinabove described, preferably being effected by introducing the condensate into the melt chlorination zone. The oxidation of the separated tars and carbon is effected at a temperature of at least 700° F., generally a temperature from 700° F. to 1200° F., and preferably a temperature from 800° F. to 900° F. The tars and carbons are combusted to carbon oxide(s) and water, and any chlorinated hydrocarbons present release chlorine values as hydogen chloride and/or chlorine.

In some cases, the condensate separated from the chlorination effluent, containing separated tars and carbon, is introduced into a stripping zone to strip chlorinated hydrocarbon therefrom, and provide a bottoms of tar and carbon dispersed in a sufficient amount of chlorinated hydrocarbon to maintain a flowable stream. In this manner, the total amount of chlorinated hydrocarbon passed to the tar and carbon oxidation steps can be controlled.

The process is generally applicable to melt chlorination processes wherein a molten salt mixture, preferably containing cuprous and cupric chloride is contacted in an oxidation reaction zone with molecular oxygen to generate copper oxychloride. In general, the oxidation reaction zone is operated at a temperature from about 600° F. to about 900° F. and a pressure in the order of from about 1 to about 20 atm. Other components, such as hydrogen chloride and/or chlorine may also be introduced into the oxidation zone.

A molten salt, containing cuprous chloride, cupric chloride and copper oxychloride is introduced into the chlorination reaction zone wherein the salt is contacted with chlorine and/or hydrogen chloride, the fresh feed to be chlorinated, and any recycle components to effect chlorination of the fresh feed. In general, such contacting is effected at a temperature of about 700° F. to about 1200° F., and a pressure of about 1 to about 20 atm. The specific temperature employed is dependent upon the fresh feed and desired products. Representative examples of such processes are described in U.S. application Ser. No. 153,374, filed June 15, 1971, which is directed to the chlorination of ethane and/or ethylene; and U.S. application Ser. No. 299,114, filed Oct. 19, 1972 and 299,848, filed Oct. 24, 1972, both of which are directed to the chlorination of methane.

The effluent withdrawn from the chlorination reaction zone is then quenched, and all or a portion of the condensed portion containing separated tars and carbon, is recycled to the chlorination reaction zone.

The remainder of the effluent is passed to a separation and recovery zone to recover net product and recycle components.

In a process for producing vinyl chloride from ethane and/or ethylene, 1,2-dichloroethane recovered from the chlorination effluent is preferably dehydrochlorinated by direct contact with molten salt, containing cuprous and cupric chloride and preferably also containing copper oxychloride. The dehydrochlorination effluent, which may include tars and carbon may also be quenched to separate tars and carbon, and all or part of the condensed portion, containing the separated tars and carbon is introduced into the chlorination zone to effect oxidation of the tars. Alternatively, if oxychloride is present in the dehydrochlorination zone, the quench liquid may be introduced into the dehydrochlorination zone to effect oxidation of the tar.

The invention will be further described with respect to the accompanying drawing which is a simplified schematic flow diagram of a process for producing vinyl chloride which incorporates the process of the present invention.

Referring now to the drawing, a molten chloride salt, such as a mixture of potassium chloride, cupric and cuprous chloride in line 201 is introduced into the top of an oxidation vessel 202, maintained at a pressure from about 1 to about 20 atm. A compressed oxygen-containing gas, such as air, in line 203, an aqueous solution of hydrogen chloride in lines 204 and 205, obtained as hereinafter described, and a by-product combustion effluent, in line 206, comprising chlorine and/or hydrogen chloride, as well as carbon oxides, water, vapor, nitrogen and perhaps unreacted oxygen, obtained as hereinafter described, are combined in line 207 and introduced into reactor 202. As a result of the countercurrent contact between the feed introduced through line 207 and the descending molten salt mixture, the salt is oxidized to produce copper oxychloride, and the hydrogen chloride and/or chlorine introduced with the combustion effluent and the hydrogen chloride introduced as aqueous hydrogen chloride are absorbed by the molten salt to produce cupric chloride. In addition, the water introduced with the aqueous hydrogen chloride is vaporized.

An effluent gas, including water vapor, nitrogen, carbon oxides, and unabsorbed hydrogen chloride rises into the top of vessel 202 wherein the effluent gas is combined with lift gas, as hereinafter described, introduced through line 208. The combined gas is directly contacted in the top of vessel 202 with a spray of aqueous hydrogen chloride quench liquid introduced through line 209 to cool the combined gas and eliminate any vaporized and entrained salts therefrom. The effluent gas is cooled to a temperature at which the molten salt is still in the form of a melt to permit the molten salt to flow back into the reactor 202.

The cooled gaseous stream, withdrawn from reactor 202, through line 211, is introduced into quench vessel 212 wherein the gaseous stream is directly contacted with an aqueous hydrogen chloride stream introduced therein through line 213. The quenching in vessel 212 also functions to separate any remaining entrained salt from the gaseous effluent. In accordance with a preferred embodiment, quenching in vessel 212 is effected in a manner to cool the effluent to a temperature from about 200° F. to about 250° F.

The remaining liquid aqueous hydrogen chloride quench liquid, containing any remaining salt, is withdrawn from vessel 212 through line 204 and introduced, as recycle feed, into reactor 202.

The effluent gas, now also containing vaporized quench liquid, withdrawn from vessel 212 through line 214 is introduced into a direct contact quench tower 215, of a type known in the art, wherein the gas is cooled by direct contact with aqueous hydrogen chloride quench liquid introduced through line 216. The quenching in tower 215 is controlled in a manner such that not all of the hydrogen chloride present in the off-gas is recovered therefrom in that such complete recovery would be accompanied by an unacceptable corresponding amount of water condensation; accordingly, condensation is preferably controlled to provide a condensed aqueous hydrogen chloride solution having a hydrogen chloride concentration from about 8 to about 20%, preferably from about 8 to about 16%, all by weight. In general, such a result can be achieved by effecting cooling in tower 215 to a temperature from about 140° F. to about 160° F.

An aqueous hydrogen chloride solution is withdrawn from tower 215 through line 217 and a first portion thereof passed through line 218, including a suitable cooler 219, for introduction into the quench tower 215 to meet the cooling requirements therefor. A second portion of the aqueous hydrogen chloride is passed through lines 209 and 213 to meet the quenching requirements of reactor 202 and of vessel 212, respectively.

The gas withdrawn from tower 215 through line 221 is caustic and water-washed in zone 222 to remove remaining hydrogen chloride, and a portion thereof released to the atmosphere through line 223. The remaining portion of the gas in line 224 is compressed in compressor 225 and the temperature thereof regulated in heat exchanger 226 prior to passage through lines 227 and 228 for use as lift gas for transporting molten salt, as hereinafter described.

The molten salt, now containing copper oxychloride, is withdrawn from the bottom of vessel 202 through line 321 and lifted by the lift gas in line 227 into a separation vessel 323 positioned adjacent the top of the reaction portion of the chlorination vessel 233. In separator 232, the molten salt is separated from the lift gas, with the molten salt being introduced into the top of the reaction portion of chlorination vessel 233 through line 234. The lift gas is withdrawn from vessel 232 through line 235, and combined with lift gas used for transporting salt to the oxidation reactor 202 for introduction into the quenching portion of vessel 202 through line 208 to thereby separate any entrained and vaporized salt therefrom.

The reaction vessel 233 is divided into two reaction sections 233a and 233b, with reaction section 233a functioning as a chlorination section and section 233b as a dehydrochlorination section. The molten salt in line 234 is introduced into both sections 233a and 233b.

Fresh feed chlorine and/or hydrogen chloride is introduced into the bottom of section 233a through line 241, and fresh feet ethane and/or ethylene, preferably ethane, is introduced in line 242 and is combined with a recycle stream comprised of ethylchloride, ethane and ethylene in line 245 for introduction into the bottom of reaction section 233a. A liquid chlorinated hydrocarbon stream, containing tars and carbon separated from the chlorination-dehydrochlorination effluent, obtained as hereinafter described, is also introduced into section 233a through line 244.

The reaction section 233a is operated at the temperatures and pressures hereinabove described to effect chlorination, dehydrogenation and dehydrochlorination of the fresh feed and recycle by direct countercurrent contact of the feed and recycle with the descending molten salt.

Recycle dichloroethane, preferably 1,2-dichloroethane, in line 250 is introduced into reaction section 233b and is countercurrently contacted with the molten salt to effect dehydrochlorination thereof to vinyl chloride.

The effluents from each of the sections 233a and 233b, each containing eqilibrium amounts of hydrogen chloride, are combined in the top portion of reactor 233.

An effluent gas, containing vinyl chloride, ethyle chloride, dichloroethane, other chlorinated hydrocarbons (one or more the following: dichloroethylenes, trichloroethylene, tetrachloroethylene, trichloroethane and tetrachloroethane) ethane, ethylene, water vapor, some hydrogen chloride, (the major portion of the hydrogen chloride produced from dichloroethane reacts with the oxychloride of the salt) carbon and tars, rises into the top of the vessel 233 wherein the effluent gas is directly contacted with a spray of quench liquid, in particular one or more of the chlorinated hydrocarbons produced in reactor 233, introduced through line 246 to cool the effluent gas and thereby eliminate any vaporized and entrained salts therefrom. The effluent gas is cooled to a temperature at which the salt mixture remains in molten salt form to permit the molten salt to flow back into the reactor 233.

The effluent gas, now containing vaporized quench liquid, is withdrawn from vessel 233 through line 247 and introduced into a quench vessel 248 wherein the effluent gas is contacted with chlorinated hydrocarbon quench liquid in line 249 to further cool the gas and thereby separate carbon, tars and any remaining entrained salts. The gas is cooled to a temperature at which tars and carbon are separated from the effluent, with essentially no aqueous hydrogen chloride being condensed therefrom. A liquid chlorinated hydrocrbon stream, containing separated tars and carbon is recycled to reactor 233 through line 244, wherein the tars are purged from the system by oxidation. The effluent gas is withdrawn from vessel 248 through line 251 and treated as hereinafter described. Alternatively, in order to reduce the quantity of chlorinated hydrocarbon returned to reactor 233, all or a portion of the condensate in line 244 is introduced through line 272 into a stripping zone 271 to strip chlorinated hydrocarbons therefrom and provide a flowable bottoms containing separated carbon and tar, which is introduced into reactor 233 through lines 273 and 244. The stripped overhead in line 274 is combined with effluent in line 251.

A molten salt is withdrawn from the bottom of reactor 233 through line 261 and lifted by lift gas in line 228 into a separation vessel 262 positioned adjacent the top of reactor 202. In separator 262, the molten salt is separated from the lift gas, and introduced through line 201 into vessel 202. The lift gas is withdrawn from separator 262 through line 264 and combined with the lift gas in line 235 for introduction into the top quenching section vessel 202 through line 208.

The reaction effluent in line 251 is cooled in condenser 310, primarily to condense a portion of the water vapor and thereby recover hydrogen chloride as an aqueous hydrogen chloride solution; the aforesaid cooling also resulting in the condensation of chlorinated hydrocarbons, including the chlorinated hydrocarbons used as quench liquid. The cooling in condenser 310 is effected to provide, as disclosed with respect to the hydrogen chloride recovery from oxidizer 202, a condensed aqueous hydrogen chloride solution having a hydrogen chloride concentration from about 8 to about 20 percent, and preferably from about 8 to about 16%, all by weight. The condensed water and chlorinated hydrocarbons are separated in a separator 311, with a water phase being withdrawn through line 312. The chlorinated hydrocarbons in line 313 are recycled through lines 246 and 249 as quench liquid for reactor 233 and quench vessel 248, respectively. The water phase comprised of aqueous hydrogen chloride in line 312 is stripped of entrained and dissolved chlorinated hydrocarbon in a stripping column 314, of a type known in the art, including an overhead condenser 315 and reflux drum 316. The overhead withdrawn from stripper 314 through line 317 is condensed in condenser 315 and introduced into drum 316. Any water withdrawn with the overhead is separated in drum 316 and recycled to stripper 314 through the line 318. The chlorinated hydrocarbons are recovered in line 319 and combined with the chlorinated hydrocarbons in line 313. Alternatively, the oil stripper 314 could also be employed to effect some concentration of the aqueous hydrogen chloride by removing from the system a portion of the water condensed from the overhead. The separated water should be treated to remove any dissolved chlorinated hydrocarbons for pollution control.

The aqueous hydrogen chloride recovered as bottoms from Column 314 in line 321 is introduced into reactor 202 through line 205 for recovery of hydrogen chloride as hereinabove described.

The remainder of the gaseous effluent from vessel 311 in line 316 is then introduced into a separation and recovery section, schematically indicated as 325 to recover the various components therefrom.

Vinyl chloride is recovered as reaction product from separation and recovery section 325. Ethane, ethylene and ethylchloride recovered in separation and recovery section 325 are recycled to reactor 233 through line 245 for ultimate conversion to vinyl chloride. Dichloroethane preferably only 1,2-dichloroethane, produced in chlorination section 233a is recovered in separation and recovery section 325 are recycled to reactor 233 through line 245 for ultimate conversion to vinyl chloride. Dichloroethane preferably only 1,2-dichloroethane, produced in chlorination section 233a is recovered in separation and recovery section 325 and recycled through line 250 to section 233b.

Other chlorinated hydrocarbons comprised of one or more of the following chlorinated hydrocarbons: dichloroethylenes, trichloroethylene, tetrachloroethylene, trichloroethanes and tetrachloroethanes recovered in separation and recovery section 325 in line 331 are introduced into a combustion chamber schematically indicated as 332 along with air in line 333, and a combustion effluent including hydrogen chloride, chlorine, carbon oxides, water vapor and nitrogen, and optionally oxygen, is withdrawn from the combustion chamber through line 334 for introduction into reactor 202 through line 206 as hereinabove described. The details of this recovery are described in Application Serial No. 95,030, filed Dec. 4, 1970, which matured into U.S. Pat. No. 3,879,481, granted on Apr. 22, 1975.

Although the present invention has been particularly described with respect to the production of vinyl chloride in a system employing two reactors, the teachings of the invention are equally applicable to the other embodiments for producing vinyl chloride. Thus, for example, the chlorination and dehydrochlorination could be effected in a single zone. Similarly, separate reactors could be used for effecting the dehydrochlorination and chlorination reactions. Furthermore, the effluents from dehydrochlorination and chlorination may be separately quenched to separate tars and carbon.

Similarly, the separated tars and carbon could be directly contacted with molten salt in a separate reactor designed and operated for such a purpose.

As a further modification, separated tars and carbon could be combusted in the oxidation vessel.

It is also to be understood that the present invention is also applicable to the chlorination of hydrocarbons other than ethane and/or ethylene. Thus, for example, the hereinabove described embodiment is also suitable for the chlorination of methane, with reactor 233 being comprised of a single reaction section for chlorination of fresh methane feed.

Numerous modifications and variations of the present invention are possible in light of the above teachings and, therefore, within the scope of the appended claims the invention may be practised otherwise than as particularly described.

What is claimed is:

1. In a process for producing a $C_1$ to $C_4$ chlorinated aliphatic hydrocarbon by contacting in a first reaction zone maintained at a temperature of from 700° F to 1200° F a $C_1$ to $C_4$ aliphatic hydrocarbon with a member selected from the group consisting of hydrogen chloride, chlorine and mixtures thereof and a molten mixture containing cuprous chloride, cupric chloride and copper oxychloride, the improvement comprising:
withdrawing from the first reaction zone a chlorinated hydrocarbon effluent, containing carbon and tars; thereafter separating carbon and tars by direct contact quenching of the chlorinated hydrocarbon effluent, said quenching effecting cooling to a temperature of from 100° F to 300° F at a pressure of from 0 to 100 psig and condensing of a portion of the chlorinated hydrocarbon, said condensed chlorinated hydrocarbon containing carbon and tars present in the effluent; and introducing at least a portion of the condensed chlorinated hydrocarbon, containing the tars and carbon into the first reaction zone to contact said molten mixture to oxidize the tars and carbon.

2. The process of claim 1 wherein the aliphatic hydrocarbon is methane and the chlorinated hydrocarbon effluent contains chlorinated $C_1$ hydrocarbons.

3. The process of claim 1 wherein the aliphatic hydrocarbon is selected from the group consisting of ethane, ethylene and mixtures thereof and the chlorinated hydrocarbon effluent contains chlorinated $C_2$ hydrocarbons.

4. The process of claim 1 wherein the chlorinated effluent is cooled to a temperature of from 150° F. to 280° F.

5. The process of claim 4 wherein the condensed chlorinated hydrocarbon is stripped of a portion of the chlorinated hydrocarbon prior to introducing condensed chlorinated hydrocarbon containing tars and carbon into the first reaction zone.

6. The process of claim 3 wherein the chlorinated hydrocarbon effluent withdrawn from the first reaction zone contains 1,2-dichloroethane and further comprising, recovering 1,2-dichloroehane from the chlorinated hydrocarbon effluent; dehydrochlorinating recovered 1,2-dichloroethane in a second reaction zone to produce a dehydrochlorination effluent; and combining the dehydrochlorination effluent with the withdrawn chlorinated hydrocarbon effluent prior to said cooling to condense chlorinated hydrocarbon.

* * * * *